United States Patent [19]
Worley et al.

[11] Patent Number: 5,948,937
[45] Date of Patent: Sep. 7, 1999

[54] METHOD FOR PRODUCING N-PHOSPHONOMETHYLGLYCINE AND ITS SALTS

[75] Inventors: Jimmy W. Worley, Creve Coeur; Melvin L. Rueppel, Kirkwood; James C. Peterson, Manchester; Sherrol L. Baysdon, St. Louis, all of Mo.

[73] Assignee: Monsanto Company, St. Louis, Mo.

[21] Appl. No.: 08/926,263

[22] Filed: Sep. 5, 1997

Related U.S. Application Data

[60] Provisional application No. 60/026,010, Sep. 12, 1996.

[51] Int. Cl.$^6$ .................................................. C07F 9/22
[52] U.S. Cl. ............................................................ 562/17
[58] Field of Search ................................................ 562/17

[56] References Cited

U.S. PATENT DOCUMENTS

| | | | |
|---|---|---|---|
| 4,221,583 | 9/1980 | Gaertner et al. | 71/86 |
| 4,369,142 | 1/1983 | Moser | 260/502.5 |
| 5,453,537 | 9/1995 | Morikawa et al. | 562/17 |
| 5,578,190 | 11/1996 | Rogers et al. | 205/436 |
| 5,679,843 | 10/1997 | Hodgkinson et al. | 562/17 |

FOREIGN PATENT DOCUMENTS

| | | | |
|---|---|---|---|
| 0 081 459 | 6/1983 | European Pat. Off. | C07F 9/38 |
| 0 186 648 | 7/1986 | European Pat. Off. | C07F 9/38 |
| 0 537 786 | 4/1993 | European Pat. Off. | C07F 9/38 |
| 62-61992 | 3/1987 | Japan . | |
| 156933 | 4/1992 | Poland | C07F 9/38 |
| 504479 | 7/1981 | Spain | C07C 143/21 |
| 545456 | 7/1985 | Spain | C07F 9/40 |
| 96/15135 | 5/1998 | WIPO | C07F 9/38 |

OTHER PUBLICATIONS

Chemical Abstracts, Abstract No. 120064–ES 545,455, vol. 106, No. 15, Otal Olivan, J.V. et al., (1987) "N–Phosphomethylglycine." XP002015599.

Chemical Abstracts, Abstract No. 160561–PL 156,933, vol. 119, No. 15, Soroka M., (1993) Preparation of N–(1–phosphonyl)glycines,especially N–(phosphonylemethyl)glycines. XP002042118.

*Primary Examiner*—Brian M. Burn
*Assistant Examiner*—Brian J. Davis
*Attorney, Agent, or Firm*—Arnold, White & Durkee

[57] ABSTRACT

This invention relates to a process for the preparation of N-phosphonomethylglycine and its salts. More particularly, this invention is directed to a method for preparing N-phosphonomethylglycine involving the reaction of AMPA, an alkali metal cyanide or hydrogen cyanide, and formaldehyde and hydrolyzing the product of that reaction to form N-phosphonomethylglycine and its salts.

24 Claims, No Drawings

METHOD FOR PRODUCING N-PHOSPHONOMETHYLGLYCINE AND ITS SALTS

This application claims the benefit of provisional application Ser. No. 60/026,010, filed Sep. 12, 1996.

BACKGROUND OF THE INVENTION

N-phosphonomethylglycine, known also by its common name glyphosate, is a highly effective commercial herbicide (available under the trade name Roundup™) useful for the control of a large variety of weeds. When used in a herbicidal composition, N-phosphonomethylglycine is generally in the form of one of its various salts in solution, preferably an aqueous solution.

Many methods for producing N-phosphonomethylglycine are known including several methods for producing N-phosphonomethylglycine from aminomethylphosphonic acid (AMPA) or its salts. These methods include a process in which AMPA is added to an aqueous solution of glyoxal at 40° to 45° C. and heated, as disclosed in Japanese Patent Application Laid-Open No. 61992/1987; a process in which AMPA and glyoxal are reacted in the presence of sulfur dioxide, as disclosed in European Patent No. 81,459 and U.S. Pat. No. 4,369,142; a process in which AMPA and glyoxylic acid are reacted and reduced subsequently with hydrogen in the presence of a palladium catalyst, as described in European Patent No. 186,648; a process in which AMPA and chloroacetic acid are heated in the presence of an acid acceptor such as sodium hydroxide, as described in Polish Patent No. 120,759 and Spanish Patent No. 504,479; and a process in which AMPA and diethyl bromomalonate are reacted under alkaline conditions, and then hydrolyzed under acidic conditions using sulfuric acid, as described in Spanish Patent No. 545,456. These processes, however, have deficiencies, including the use of volatile gases, creation of high levels of waste by-products, insufficient product yield, relatively high materials cost, and inadequate product quality.

Other known processes for preparing N-phosphonomethylglycine from AMPA involve the hydrolysis of the intermediate material N-phosphonomethylglycinonitrile or its salts. For example, in U.S. Pat. No. 4,221,583, AMPA is reacted sequentially with formaldehyde, generally in the presence of alkali, and an alkali metal cyanide at pH 7 to 10. The resulting product, N-phosphonomethylglycinonitrile, is then converted to N-phosphonomethylglycine. The yield of isolated N-phosphonomethylglycine, based on AMPA, was only about 60% and it was necessary to use up to 2.4 times the molar equivalent of potassium cyanide and to control the pH carefully to accomplish this yield.

Similarly, in Polish Patent No. 156,933, the reaction of AMPA to prepare N-phosphonomethylglycinonitrile is sequential and multi-step using formaldehyde and an alkali metal cyanide or hydrogen cyanide. Polish Patent No. 156,933 requires even more careful control of pH by adding mineral acid in order to obtain optimum yields.

PCT/95/GB2573 is also directed to a reaction of AMPA to prepare N-phosphonomethylglycinonitrile in a sequential, multi-step process using formaldehyde and an alkali metal cyanide. PCT/95/GB2573 avoids the use of hydrogen cyanide (HCN) and also requires careful control of pH by continuously adding mineral acid to obtain optimum yields.

U.S. Pat. No. 5,453,537 further discloses a process for preparing N-phosphonomethylglycine using AMPA as a starting compound. An AMPA, in the form of its dialkali metal salt, and glycolonitrile are reacted and the resulting N-phosphonomethylglycinonitrile is hydrolyzed to produce N-phosphonomethylglycine. According to the examples, the yield of isolated N-phosphonomethylglycine was at best 78% based on AMPA. The nature of AMPA for this process requires the addition of an alkali metal hydroxide in an amount of 2 times the molar amount of AMPA for reaction to occur between glycolonitrile and AMPA. Using glycolonitrile to produce the intermediate N-phosphonomethylglycinonitrile in this process also precludes the direct cyanomethylation of AMPA by the use of more basic, more readily available, and less expensive raw materials such as formaldehyde and sodium, potassium or hydrogen cyanide.

Thus, there is a need in the art for a versatile process which directly and readily converts AMPA to N-phosphonomethylglycine and its salts in high yields from inexpensive and available raw materials.

SUMMARY OF THE INVENTION

This invention relates to a process for the preparation of N-phosphonomethylglycine and its salts. More particularly, this invention is directed to a method for preparing N-phosphonomethylglycine involving the reaction of AMPA, an alkali metal or hydrogen cyanide, and formaldehyde and hydrolyzing the product of that reaction to form N-phosphonomethylglycine and its salts.

The process according to the invention offers the significant advantage over other N-phosphonomethylglycine formation processes involving the cyanomethylation of AMPA in that it does not require rigorous attention to pH. In particular there is no need to add a mineral acid to the reaction solution of AMPA/alkali metal hydroxide/alkali metal or hydrogen cyanide/formaldehyde in order to control pH. The use of the alkali metal or hydrogen cyanide and formaldehyde reactants in the inventive AMPA cyanomethylation process also allows the reaction to proceed without the use of a preformed glycolonitrile reactant as used in some other processes. Additionally, the inventive method is not limited to alkali metal cyanide reactants as it may use hydrogen cyanide (HCN) as the cyanide reactant.

DESCRIPTION OF ILLUSTRATIVE EMBODIMENTS

The invention is broadly directed to a step of cyanomethylating AMPA in the production of N-phosphonomethylglycine.

In a preferred embodiment, the inventive process is directed to a reaction of AMPA, about one equivalent of an alkali metal hydroxide, about one equivalent of an alkali metal or hydrogen cyanide, and about one equivalent of formaldehyde; followed by the addition of about one equivalent of alkali metal hydroxide; and subsequent acidification of the mixture to crystallize the glyphosate product.

In a further preferred embodiment, the process according to the invention involves a continuous process wherein AMPA and about one equivalent of an alkali metal hydroxide (the mixture of which forms the mono-salt of AMPA), about one equivalent of hydrogen or alkali metal cyanide, and about one equivalent of formaldehyde are added to a reactor at about the same molar rate over a time period, e.g., about 40 to 50 minutes, keeping the temperature of the mixture low, e.g., at about 5° C. or lower. The reaction solution is then stirred, e.g., for about 30 minutes at about 3–5° C., and then stirred at ambient temperature for a period of time, e.g., for about 1.5 hours. About one equivalent of alkali metal hydroxide is then added to the solution and heated, e.g., for about 2 hours. The solution is then cooled and acidified to a pH such that the glyphosate product crystallizes, e.g. at about pH 1.05, and the glyphosate product that crystallizes is removed by filtration or centrifugation.

In another preferred embodiment, the process according to the invention involves a batch process wherein a monosalt of AMPA (which may be formed by a mixture of AMPA and an equivalent of an alkali metal hydroxide) and an equivalent of an alkali metal or hydrogen cyanide are mixed in a reactor in an aqueous solution; to which an equivalent of formaldehyde solution is added over a period of time, keeping the temperature below about 25° C., after which the solution is stirred at ambient temperature for some period of time, e.g., about 1–3 hours. About one equivalent of alkali metal hydroxide is subsequently added to the mixture and heated to reflux for a period of time, e.g., 1–3 hours. The solution is then cooled and acidified to a pH such that the glyphosate product crystallizes, e.g. at about pH 1.05, and the glyphosate product that crystallizes is removed by filtration or centrifugation.

The reaction of aminomethylphosphonate, an alkali metal cyanide or hydrogen cyanide, and formaldehyde may be carried out at a temperature not exceeding 60° C.

Mineral acid may be added to effect hydrolysis of N-phosphonomethylglycinonitrile.

Alternatively, N-phosphonomethylglycine or its salts may be prepared by a process comprising the steps of: concurrently mixing at least two of the reactants of an aminomethylphosphonate, an alkali metal cyanide or hydrogen cyanide, and formaldehyde; subsequently adding the other reactants to form a product, whereby substantially no pH control is required during the formation of said product; hydrolyzing said product, and isolating the hydrolyzed product to obtain N-phosphonomethylglycine or its salts. One embodiment includes concurrently mixing formaldehyde and an alkali metal cyanide or hydrogen cyanide, and then reacting the mixture with aminomethylphosphonic acid. The aminomethylphosphonic acid may be further reacted with an alkali metal hydroxide. An alternative embodiment includes concurrently mixing formaldehyde, alkali metal hydroxide, and aminomethylphosphonic acid, and then reacting the mixture with an alkali metal cyanide or hydrogen cyanide. A further alternative embodiment involves the concurrent mixing of an alkali metal cyanide or hydrogen cyanide and formaldehyde, and then reacting the mixture with a monoalkali metal aminomethylphosphonate. Yet an additional alternative embodiment involves the concurrent mixing of an alkali metal cyanide, an alkali metal hydroxide and aminomethylphosphonic acid, and then reacting the mixture with formaldehyde.

The "AMPA" reactant is generally aminomethylphosphonic acid or a salt thereof, also referred to as "an aminomethylphosphonate". For example the AMPA may be a mono- or di-alkali metal salt of aminomethylphosphonic acid. In a preferred embodiment, the AMPA reactant is the mono-alkali metal salt of AMPA, e.g., the monosodium- or monopotassium-salt of AMPA, which may be prepared by mixing aminomethylphosphonic acid with an equivalent of an alkali metal hydroxide. For example, the mono-sodium salt of AMPA may be prepared by mixing AMPA and an equivalent of sodium hydroxide, by themselves or in the presence of other reactants, e.g. an alkali metal or hydrogen cyanide or formaldehyde.

The cyanide reactant may be either an alkali metal cyanide, e.g., sodium cyanide or potassium cyanide, or hydrogen cyanide. The formaldehyde reactant may be added in the form of formalin. The AMPA/alkali metal or hydrogen cyanide/formaldehyde reactants are preferably added in a molar ratio of about 1:1:1. Where the AMPA component is a mixture of aminomethylphosphonic acid and an alkali metal hydroxide, the molar ratio of aminomethylphosphonic acid/alkali metal hydroxide/alkali metal or hydrogen cyanide/formaldehyde is about 1:1:1:1. In this context, the ratio of "about 1:1" preferably means a molar ratio of 0.75–1.25:1, more preferably a molar ratio of 0.85–1.15:1, and most preferably a molar ratio of 0.9–1.1:1.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

A 250 mL 3-neck flask containing 25 mL water was cooled in an ice bath and equipped with a thermometer, a mechanical stirrer and two syringe pumps. One pump had two syringes. A solution of sodium cyanide (4.9 g; 0.1 mol) in 14 mL water was taken up into one while the other contained 37% ACS grade formalin (0.1 mol) in 14 mL water. A 60 mL syringe was mounted on the other pump. This syringe was used to add the AMPA as its monosodium salt prepared from AMPA (11.1 g; 0.1 mol) dissolved in 60 mL water with sodium hydroxide pellets (0.1 mol) at ambient temperature. With the monosodium salt of AMPA, the solution was gently warmed to maintain solubility.

The syringe pumps were started simultaneously. The three reactants were thereby transferred into the flask at about the same molar rate over 40 to 50 minutes and each syringe rinsed with 2 mL water. The temperature during the addition was kept at 5° C. or lower during most of the addition. The reaction solution was then stirred at 30° to 5° C. for about 30 minutes and then at ambient temperature for about 1.5 hours.

A 1.0 mL aliquot of the reaction mixture was weighed to four decimal places and diluted with water in a 10 mL volumetric flask. Phosphorus NMR of this diluted sample using the coaxial external standard of 5% $H_3PO_4$ was obtained. The chemical shifts of AMPA and N-cyanomethyl-AMPA (i.e., N-phosphonomethylglycinonitrile) were 19.1 and 16.2 ppm relative to phosphoric acid in the presence of 3.0 equivalents of NaOH. In this case, the bis-cyanomethylated AMPA derivative was assigned as a shoulder on the N-cyanomethyl AMPA peak at 16.4 ppm. With two equivalents of NaOH, the chemical shifts of N-cyanomethyl-AMPA and unreacted AMPA were observed at 14.9–15.0 and 15.9–16.2 ppm respectively. The NMR results indicated a yield of N-phosphonomethylglycinonitrile of 94.6%.

Sodium hydroxide pellets (100 mmol) were added to the solution. The resulting yellow solution was then heated at reflux for 2 hours with ammonia offgassing.

After cooling to ambient temperature, a 1.0 mL aliquot of the hydrolysate was weighed to four decimal places and diluted with water in a 10 mL volumetric flask. The resulting solution was analyzed by the 31 P NMR method. The chemical shifts of AMPA, glyphosate and GI in these hydrolysate samples were 18.7–18.9, 15.9–16.2 and 15.4–16.1 ppm relative to phosphoric acid, respectively. The NMR results indicated a yield of 94.6%.

The yellow hydrolysate was transferred to a tared 250 mL flask, weighed and concentrated in vacuo on a rotary evaporator at 50–65° C. depending on the pressure. The concentrated hydrolysate was weighed, transferred back to the original flask and the weight adjusted to give a total amount of concentrated hydrolysate of approximately 65 grams by adding water. The concentrated hydrolysate was mechanically stirred, cooled in an ice bath and treated with three portions of 37% HCl to give a pH of 1.05 in the acidified solution. After crystallization the slurry was stirred at ambient temperature overnight and the pH checked periodically with small amounts of concentrated 37% HCl or aqueous NaOH (40 or 50 wt %) added to adjust the pH to 1.05±0.05. When the pH remained within this pH range for at least one hour, the crystallization was assumed to be complete.

The slurry was suction filtered into a glass sintered funnel mounted on a tared 250 mL vacuum filter flask. The initial filtrate was re-used to rinse out the flask and ensure complete solid transfer. The filter cake was washed successively with 10 mL water and 10 mL methanol. The wet cake was dried in the vacuum oven at 45–55° C. until the weight of cake was constant. The dried cake and filtrate were assayed for glyphosate using HPLC. The isolated yield of glyphosate was 85.3% with a purity of 98.8%.

Example 2

A 250 mL 3-neck flask was cooled in an ice bath and equipped with a thermometer, a mechanical stirrer and a syringe pump with two syringes. A solution of sodium cyanide (4.9 g; 0.1 mol) in 14 mL water was taken up into one while the other contained 37% ACS grade formalin (0.1 mol) in 14 mL water. The monosodium salt of AMPA (0.1 mol) in 60 mL water was charged to the 250 mL flask and the formaldehyde and sodium cyanide solutions were added simultaneously at a rate of 0.6 mL/min at 3–5° C. The reaction mixture was then stirred at 3–5° C. and then at ambient temperature as summarized for Example 1.

Phosphorus NMR of this sample according to Example 1 indicated a yield of N-phosphonomethylglycinonitrile of 93.7%.

The hydrolysis, HCl acidification, and isolation of glyphosate solid were run as described in Example 1. The NMR results indicated a yield of N-phosphonomethylglycine of 91.1%. The isolated yield of glyphosate was 82% with a purity of 100.0%.

Example 3

The procedure of Example 2 was repeated except that the flask was charged with sodium hydroxide pellets (75 mmol) and AMPA (100 mmol) in 60 mL water in place of the monosodium salt of AMPA and sodium hydroxide (125 mmol) was added to effect hydrolysis.

Phosphorus NMR of this sample according to Example 1 indicated a yield of N-phosphonomethylglycinonitrile 51.2%. The NMR results indicated a yield of N-phosphonomethylglycine of 56.8%. The isolated yield of N-phosphonomethylglycine was 40.8% with a purity of 50%.

Example 4

The procedure of Example 2 was repeated except that the flask was charged with sodium hydroxide pellets (125 mmol) and AMPA (100 mmol) in 60 mL water in place of the monosodium salt of AMPA and sodium hydroxide (75 mmol) was added to effect hydrolysis.

Phosphorus NMR of this sample according to Example 1 indicated a yield of N-phosphonomethylglycinonitrile 80.2%. The NMR results indicated a yield of N-phosphonomethylglycine of 80.6%. The isolated yield of N-phosphonomethylglycine was 67% with a purity of 92%.

Example 5

To prepare an aqueous mixture of sodium cyanide and formaldehyde, a 50 mL 3-neck flask was equipped with a magnetic stirrer, a thermometer, and a 10 mL plastic disposable syringe driven by a pump. A magnetically stirred solution of sodium cyanide (4.9 g; 0.1 mol) in 15 mL milli-Q water in the flask was cooled in an ice bath to 5° C. ACS reagent grade formalin solution (37%; 7.5 mL; 0.1 mol) was added dropwise from the syringe at a rate of 0.2 mL/min maintaining a temperature of 5 and 10° C. At the end of the addition, the solution was cooled and kept at 5° C.

A 250 mL 3-neck flask was equipped with a mechanical stirrer, a Y-adapter with a thermometer, a syringe pump with a 20 mL syringe and a reflux condenser. A mechanically stirred slurry of AMPA (11.1 g; 0.1 mol) in 60 mL water was cooled in an ice bath and treated with a specified amount of sodium hydroxide pellets (100 mmol). The sodium hydroxide pellets were dissolved with stirring and the resulting solution cooled to 5° C.

The aqueous mixture of sodium cyanide and formaldehyde prepared above was added to the AMPA solution prepared above with the syringe pump at a rate of about 0.6 mL/min keeping the temperature below about 5° C. At the end of the addition, the reaction mixture was stirred at 3–5° C. for an additional 30–45 minutes. The ice bath was removed and the tinted reaction mixture was stirred for an additional 90–100 minutes at ambient temperature. Phosphorus NMR indicated a yield of N-phosphonomethylglycinonitrile of 94.1% and 100% in two separate runs.

The hydrolysis, HCl acidification and isolation of glyphosate solid from these experiments were the same as that described for Example 1. The NMR results indicated yields of N-phosphonomethylglycine of 94.9% and 93.1% in the two runs. The corresponding isolated yields of glyphosate were 84.1% and 81.9% with a respective purity of 98.7% and 95.4%.

Example 6

The procedure of Example 5 was repeated except that sodium hydroxide pellets (100 mmol) were dissolved in an aqueous mixture of sodium cyanide and formaldehyde and no additional sodium hydroxide was added to effect hydrolysis. Phosphorus NMR indicated a yield of N-phosphonomethylglycinonitrile of 51.8%. NMR results indicated a yield of N-phosphonomethylglycine of 73.7%. The corresponding isolated yield of glyphosate was 56.9% with a purity of 69.7%.

Example 7

The procedure of Example 6 was repeated except that AMPA (100 mmol) was used instead of monosodium aminomethylphosphonate and additional sodium hydroxide (100 mmol) was added to effect hydrolysis. Phosphorus NMR indicated a yield of N-phosphonomethylglycinonitrile of 93.0%. NMR results indicated a yield of N-phosphonomethylglycine of 92.6%. The corresponding isolated yield of glyphosate was 79.6% with a purity of 94.7%.

Examples 8 to 13

The procedure of Example 5 was repeated except that the amount of sodium hydroxide pellets used to dissolve AMPA prior to addition to the reaction flask and the amount of additional sodium hydroxide added to effect hydrolysis were varied as shown in Table 1 along with the results of said variations.

Example 14

According to the procedure of Example 1, the disodium salt of AMPA, prepared in 60 mL water from AMPA (11.1 g; 0.1 mol) with sodium hydroxide pellets (0.2 mol), was used in place of its monosodium salt.

Phosphorus NMR of the reaction mixture according to Example 1 indicated a yield of N-phosphonomethylglycinonitrile of 54.6%.

The hydrolysis was run as described in Example 1 except that no sodium hydroxide was added. The HCl acidification and isolation of glyphosate solid were run as described in Example 1. The NMR results indicated a yield of N-phosphonomethylglycine of 71.3%. The isolated yield of glyphosate was 54.8% with an assay of 69.6%.

Example 15

A 250 mL 3-neck flask equipped with a thermometer, a mechanical stirrer and a syringe pump with a syringe containing 37% ACS grade formalin (0.1 mol) in 7.5 mL water. The monosodium salt of AMPA (0.1 mol) and sodium cyanide (4.9 g; 0.1 mol) in 120 mL water was charged to the 250 mL flask and kept at a temperature of less than 5° C. The formaldehyde was added at a rate of 0.2 mL/min. The reaction mixture was then stirred at 3–5° C. and ambient temperature as summarized for Example 1.

Phosphorus NMR of this sample according to Example 1 indicated a yield of N-phosphonomethylglycinonitrile of 94.1%.

The hydrolysis, HCl acidification and isolation of glyphosate solid were run as described in Example 1. The NMR results indicated a yield of N-phosphonomethylglycine of 96.7%. The isolated yield of glyphosate was 86.7% with a purity of 100.0%.

Example 16

The procedure of Example 15 was repeated except that the monosodium salt of AMPA (0.1 mol) and sodium cyanide (0.1 mol) were charged to the flask and kept at an ambient temperature of 25° C. The formaldehyde was added at a rate of 0.2 mL/min at 25° C. The reaction mixture was then stirred at ambient temperature as summarized for Example 1.

Phosphorus NMR of this sample according to Example 1 indicated a yield of N-phosphonomethylglycinonitrile of 82.8%.

The hydrolysis, HCl acidification and isolation of glyphosate solid were run as described in Example 1. The NMR results indicated a yield of N-phosphonomethylglycine of 97.3%. The isolated yield of glyphosate was 81.5% with a purity of 95.7%.

Example 17

The procedure of Example 15 was repeated except that the monosodium salt of AMPA (0.1 mol) and sodium cyanide (0.1 mol) were charged to the flask in 60 mL water and kept at a temperature of less than 5° C. The formaldehyde was added at a rate of 0.2 mL/min. The reaction mixture was then stirred at 3–5° C. and ambient temperature as summarized for Example 1.

Phosphorus NMR of this sample according to Example 1 indicated a yield of N-phosphonomethylglycinonitrile of 89.6%.

The hydrolysis, HCl acidification and isolation of glyphosate solid were run as described in Example 1. The NMR results indicated a yield of N-phosphonomethylglycine of 93.4%. The isolated yield of glyphosate was 80.5% with a purity of 94.8%.

Example 18

A 250 mL 3-neck flask equipped with a thermometer, a mechanical stirrer and a syringe pump with a syringe containing an aqueous solution of sodium cyanide (4.9 g; 0.1 mol) in 12 mL water. The monosodium salt of AMPA (0.1 mol) in 60 mL water and 37% ACS grade formalin (0.1 mol) in 7.5 mL water was charged to the 250 mL flask and kept at a temperature of less than 5° C. The sodium cyanide solution was added at a rate of 0.32 mL/min. The reaction mixture was then stirred at 3–5° C. and ambient temperature as summarized for Example 1.

Phosphorus NMR of this sample according to Example 1 indicated a yield of N-phosphonomethylglycinonitrile of 79.4%.

The hydrolysis, HCl acidification and isolation of glyphosate solid were run as described in Example 1. The NMR results indicated a yield of N-phosphonomethylglycine of 79.0%. The isolated yield of glyphosate was 67.0% with a purity of 92.4%.

Example 19

A 250 mL 3-neck flask was equipped with a mechanical stirrer, a thermometer, and a syringe pump. A magnetically stirred solution of sodium cyanide (4.9 g; 0.1 mol) in 35 mL milli-Q water was added and cooled in an ice bath to 4° C. 37% ACS reagent grade formalin solution (7.5 mL; 0.1 mol) was added dropwise from the syringe at a rate of 0.2 mL/min, keeping the temperature between 5–10° C.

In a separate 125 mL Erlenmeyer flask, a magnetically stirred slurry of AMPA (11.1 g; 0.1 mol) in 60 mL water was cooled in an ice bath and treated with sodium hydroxide (100 mmol) to make a solution of the monosodium salt of AMPA. The ice bath was removed and the tinted solution was allowed to warm to room temperature. This solution was added to the flask at 5° C. using the syringe pump at a flow rate of about 1.3 mL/min. The reaction mixture was then stirred at 5° C. or less for ½ hour and then at ambient temperature for 1.4 hours.

Phosphorus NMR of this sample according to Example 1 indicated a yield of N-phosphonomethylglycinonitrile of 95.6%.

The hydrolysis, HCl acidification and isolation of glyphosate solid were run as described in Example 1. The NMR results indicated a yield of N-phosphonomethylglycine of 94.2%. The isolated yield of glyphosate was 82.4% with a purity of 96.7%.

TABLE 1

| Example Number | 8 | 9 | 10 | 11 | 12 | 13 |
|---|---|---|---|---|---|---|
| NaOH (mmol) for AMPA | 75 | 125 | 150 | 200 | 200 | 200 |
| NaOH (mmol) for Hydrolysis | 125 | 75 | 50 | 0 | 0 | 0 |
| PMGN Yield (%) | 76.4 | 71.9 | 65.4 | No Data | 49.2 | No Data |
| PMG NMR Yield (%) | 80.7 | 79.1 | 79.1 | 71.4 | 72.0 | 71.6 |
| PMG Yield Isolated (%) | 67.4 | 65.5 | 54.7 | 60.4 | 54.7 | 54.9 |
| PMG Assay (%) | 86.3 | 93.0 | 88.0 | 82.3 | 91.5 | 87.5 |

AMPA: Aminomethylphosphonic Acid
PMGN: N-Phosphonomethylglycinonitrile
PMG: N-Phosphonomethylglycine All of processes disclosed and claimed herein can be made and executed without undue experimentation in light of the present disclosure. While the compositions and methods of this invention have been described in terms of preferred embodiments, it will be apparent to those of skill in the art that variations may be applied to the process described herein without departing from the concept, spirit and scope of the invention. All such similar substitutes and modifications apparent to those skilled in the art are deemed to be within the spirit, scope and concept of the invention.

What is claimed is:

1. A process for preparing N-phosphonomethylglycine or its salts, comprising the steps of:
   concurrently mixing an aminomethylphosphonate, an alkali metal cyanide or hydrogen cyanide, and formaldehyde to form a product,
   hydrolyzing said product, and
   isolating the hydrolyzed product to obtain N-phosphonomethylglycine or its salts.

2. A process as in claim 1, wherein the aminomethylphosphonate is the mono-salt of aminomethylphosphonic acid.

3. A process as in claim 2, wherein the mono-salt of aminomethylphosphonic acid is the mono-sodium or mono-potassium salt.

4. A process as in claim 1, wherein the alkali metal cyanide or hydrogen cyanide is hydrogen cyanide.

5. A process as in claim 1, wherein the alkali metal cyanide is potassium cyanide or sodium cyanide.

6. A process as in claim 1, wherein the reaction of aminomethylphosphonate, an alkali metal cyanide or hydrogen cyanide, and formaldehyde requires substantially no pH control.

7. A process as in claim 1, wherein the reaction of aminomethylphosphonate, an alkali metal cyanide or hydrogen cyanide, and formaldehyde is carried out at a temperature not exceeding 60° C.

8. A process as claimed in claim 1, wherein formaldehyde is used in an amount of about 0.75 to 1.25 times the molar amount relative to the aminomethylphosphonate.

9. A process as claimed in claim 1, wherein an alkali metal cyanide or hydrogen cyanide is used in an amount of about 0.75 to 1.25 times the molar amount relative to the aminomethylphosphonate.

10. A process as claimed in claim 1, wherein the aminomethylphosphonate is aminomethylphosphonic acid, a monoalkali metal aminomethylphosphonate or a dialkali metal aminomethylphosphonate.

11. A process as claimed in claim 1, wherein the aminomethylphosphonate is the product of aminomethylphosphonic acid and an alkali metal hydroxide.

12. A process as in claim 11, wherein the alkali metal hydroxide is sodium hydroxide or potassium hydroxide.

13. A process as in claim 11, wherein an alkali metal hydroxide is used in an amount from about 0.75 to about 1.25 times the molar amount relative to the aminomethylphosphonic acid.

14. A process as in claim 1, wherein a mineral acid added is added to effect the hydrolysis.

15. A process as claimed in claim 1, wherein N-phosphonomethylglycine is obtained following hydrolysis by adding an alkali metal hydroxide or strong mineral acid in an amount sufficient to give a pH of about 1.0 to 1.2.

16. A process as claimed in claim 1, wherein aminomethylphosphonic acid, an alkali metal hydroxide, formaldehyde, and an alkali metal cyanide or hydrogen cyanide are concurrently added.

17. A process as claimed in claim 1, wherein a monoalkali metal aminomethylphosphonate, formaldehyde, and alkali metal cyanide are concurrently added.

18. A process as claimed in claim 1, wherein a dialkali metal aminomethylphosphonate, formaldehyde, and hydrogen cyanide are concurrently added.

19. A process for preparing N-phosphonomethylglycine or its salts, comprising the steps of:
   concurrently mixing at least two of the reactants of an aminomethylphosphonate, an alkali metal cyanide or hydrogen cyanide, and formaldehyde;
   subsequently adding the other reactants to form a product, whereby substantially no pH control is required during the formation of said product;
   hydrolyzing said product, and
   isolating the hydrolyzed product to obtain N-phosphonomethylglycine or its salts.

20. A process as claimed in claim 19, wherein formaldehyde and an alkali metal cyanide or hydrogen cyanide are concurrently mixed and then reacted with aminomethylphosphonic acid.

21. A process as in claim 20, where the aminomethylphosphonic acid is further reacted with an alkali metal hydroxide.

22. A process as claimed in claim 19, wherein formaldehyde, alkali metal hydroxide, and aminomethylphosphonic acid are concurrently mixed and then reacted with an alkali metal cyanide or hydrogen cyanide.

23. A process as claimed in claim 19, wherein an alkali metal cyanide or hydrogen cyanide and formaldehyde are concurrently mixed together and then reacted with a monoalkali metal aminomethylphosphonate.

24. A process as claimed in claim 19, wherein an alkali metal cyanide, an alkali metal hydroxide and aminomethylphosphonic acid are concurrently mixed together and then reacted with formaldehyde.

* * * * *